Jan. 22, 1974 B. J. MACHIN Plant Pat. 3,445
CHRYSANTHEMUM PLANT
Filed Dec. 27, 1971
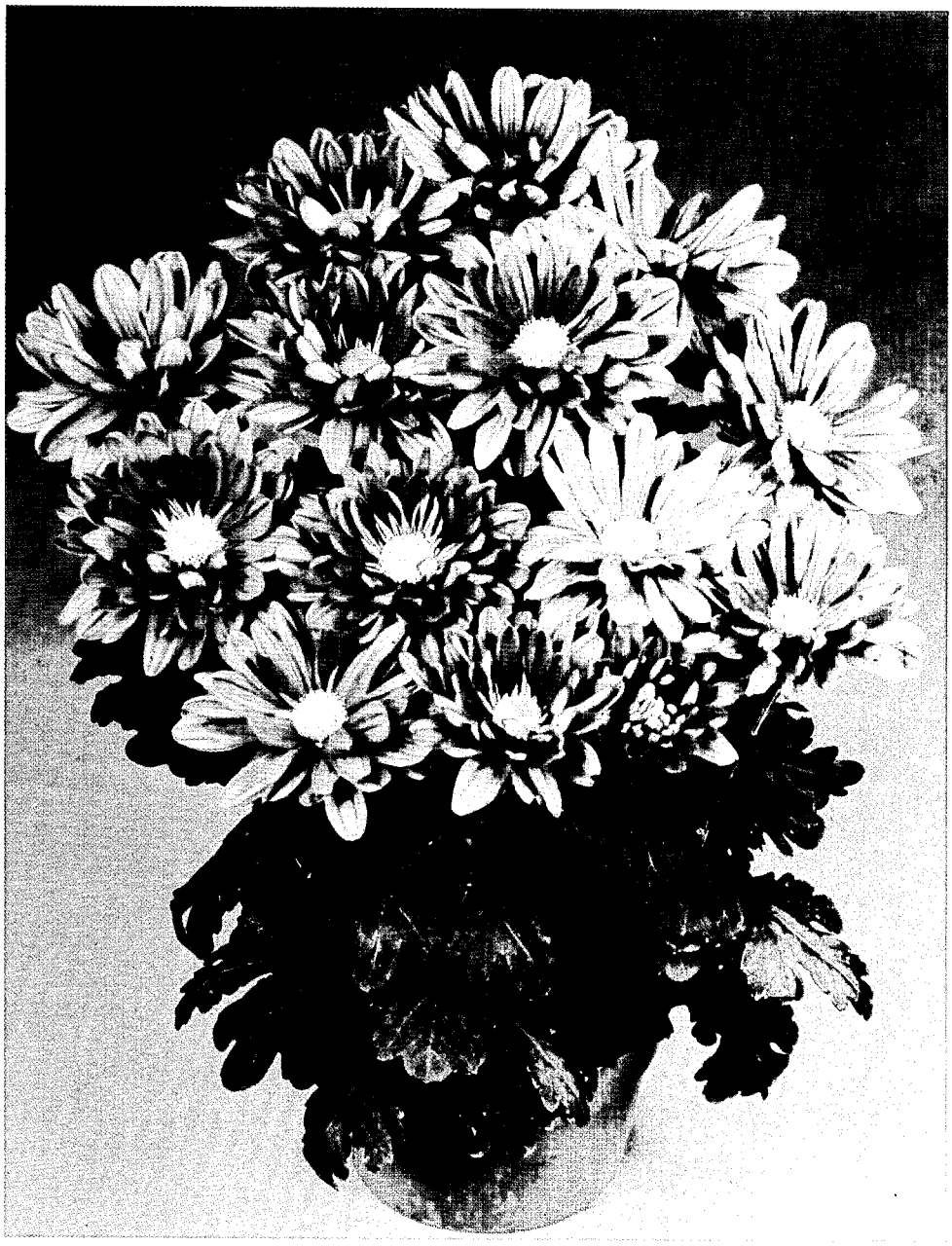

United States Patent Office

Plant Pat. 3,445
Patented Jan. 22, 1974

3,445
CHRYSANTHEMUM PLANT

Barrie John Machin, East Broyle Estate, Chichester, England, assignor to Frampton's Nurseries Limited, Chichester, Sussex, England Filed Dec. 27, 1971, Ser. No. 212,833
Int. Cl. A01h 5/00
U.S. Cl. Plt.—74 1 Claim This invention relates to a new and distinctive variety of *Chrysanthemum morifolium* Bailey (spray type) known as Bronze Nero.

Bronze Nero is a sport from the unpatented variety Nero, which is a seedling originated by me from a cross made in 1967 between the unpatented variety Tuneful and the unpatented variety Delight, the former being the seed parent, and the latter being the pollen parent.

The variety Nero resulted from an extensive breeding program with the object of producing improved varieties for year round chrysanthemum production programs with more vigor and reduced flowering time compared with existing varieties. The immediate objective was to improve the varieties Tuneful and Delight, which in Southern England required a total of 13 or 14 weeks for single stem flowering during the summer.

The variety Bronze Nero is a sport induced by irradiation from Nero in October 1969.

Bronze Nero is distinguished from Nero by its marigold orange color, RHS 28B, with reddish undertones, as compared with the red bronze, RHS 42B, of Nero.

Bronze Nero is distinguished from Tuneful, which is, aside from Nero, the most similar variety with which I am familiar, by the following improved characteristics:

(1) It is extremely vigorous and will produce flowering crops in 12 weeks from rooted cuttings during the summer and 16 weeks from rooted cuttings during the winter.
(2) Despite its extreme vigor it is also responsive and will set buds and flower uniformly in a wide range of environmental conditions.
(3) Its color is very bright, comparing favorably with other bronze singles, e.g., Tuneful, and holding well in high temperature conditions.

Asexual reproduction of this new variety Bronze Nero by rooting vegetative shoots at Frampton's Nurseries Ltd., Forbridge Nursery, Chichester, Sussex, England, shows that the above characteristics are fixed and come true to type in succeeding generations.

The accompanying drawing shows a typical flower of my new variety in color as nearly true as it is reasonably possible to make the same in a color illustration of this character.

The following is a detailed description of the new variety Bronze Nero with color terminology in accordance with the Royal Horticultural Society color chart, hereinafter referred to as RHS.

Genus: Chrysanthemum
Species: Morifolium Bailey
Type: Spray
Class: Single
Breeding: The original seedling resulted from across between the variety Tuneful, the seed parent, and Delight, the pollen parent. The cross was made in 1967 at Frampton's Nurseries, Ltd., Forbridge Nursery, Chichester, Sussex, England.
Propagation: Holds its distinguishing characteristics through succeeding propagations by rooting vegetative shoots.
Flower: When grown and observed in Sussex, England, 6 to 12 flowers are borne on pedicels after removal of the main apical bud.
Bloom:
*Size.*—Average diameter is 10 cm. when fully open.
*Petalage.*—Single—approximately 50 ray petals. Diameter of disc is 1¾ to 2 cm.
*Form.*—Single, with flat slightly reflexing petals.
*Petals.*—Long, broad, overlapping, blunt and with medium texture.
*Pedicels.*—Thick and 10 to 12 cm. in length.
Color of open bloom:
Inner face of fully expanded ray petals, RHS 28B streaked with RHS 34A.
Outer face of fully expanded ray petal, RHS 20B.
Inner face of young ray petal, RHS 34A.
Outer face of young ray petals, RHS 20B.
Inner and outer faces of disc petals, RHS 7A.
Response Group: 10 weeks.
Temperature tolerance: 55–60° F. at night.
Plant: Strong upright habit of growth.
Foliage:
Medium quality, average internode length 3 cm.
Medium to large size.
Color, RHS 137B.
Texture, medium.
Stem: Thick and strong. Color 143C at flowering—water uptake good.

I claim:

1. A new and distinct variety of *Chrysanthemum morifolium* Bailey, substantially as herein shown and described, characterized particularly as to novelty by the unique combination of a reduced flowering time, uniformity of response in a wide range of environmental conditions, and marigold orange color with red undertones.

No references cited.

ROBERT E. BAGWILL, Primary Examiner